(12) United States Patent
Russell (10) Patent No.: US 8,948,885 B2
(45) Date of Patent: Feb. 3, 2015

(54) REPOSITIONABLE ELECTRODE AND SYSTEMS AND METHODS FOR IDENTIFYING ELECTRODE POSITION FOR CARDIOTHERAPY

(75) Inventor: James K. Russell, Seattle, WA (US)

(73) Assignee: Koninklijke Philips N.V., Eindhoven (NL)

( * ) Notice: Subject to any disclaimer, the term of this patent is extended or adjusted under 35 U.S.C. 154(b) by 521 days.

(21) Appl. No.: 12/739,446

(22) PCT Filed: Nov. 3, 2008

(86) PCT No.: PCT/IB2008/054565
§ 371 (c)(1),
(2), (4) Date: Apr. 23, 2010

(87) PCT Pub. No.: WO2009/060374
PCT Pub. Date: May 14, 2009

(65) Prior Publication Data
US 2010/0234909 A1    Sep. 16, 2010

Related U.S. Application Data (60) Provisional application No. 60/986,309, filed on Nov. 8, 2007.

(51) Int. Cl.
*A61N 1/362*    (2006.01)
*A61N 1/04*    (2006.01)
*A61B 5/0464*    (2006.01)
(Continued)

(52) U.S. Cl.
CPC ............ *A61B 5/7221* (2013.01); *A61N 1/0476* (2013.01); *A61N 1/0492* (2013.01); *A61B 5/0464* (2013.01); *A61N 1/046* (2013.01); *A61N 1/3925* (2013.01)
USPC ........... 607/142; 600/509; 600/522; 600/523; 600/546; 600/547; 600/391; 600/392

(58) Field of Classification Search
CPC .................... A61B 5/7221; A61B 2017/00044
USPC ......... 600/509, 522, 523, 546, 547, 391, 392; 607/142
See application file for complete search history.

(56) References Cited

U.S. PATENT DOCUMENTS 3,961,623 A    6/1976  Milani et al.
4,653,501 A *  3/1987  Cartmell et al. .............. 600/392
4,703,380 A   10/1987  Imamura et al.
(Continued)

FOREIGN PATENT DOCUMENTS

EP    1095612 A    5/2001
GB    2368799 A    5/2002
(Continued)

*Primary Examiner* — Christopher D Koharski
*Assistant Examiner* — Natasha Patel (57) ABSTRACT

A system and method for positioning an electrode for cardiotherapy of atrial arrhythmia are described. Signals from patient electrical activity for a plurality of electrode locations on a patient are analyzed. An electrode can be repositioned to different locations on the patient to obtain signals from patient electrical activity therefrom. A human perceptible output indicative of the quality of the signals for the plurality of locations is generated and a final electrode location on the patient for placement of the electrode for cardiotherapy is identified based on the human perceptible output.

8 Claims, 11 Drawing Sheets

(51) Int. Cl.
*A61N 1/39* (2006.01)
*A61B 5/00* (2006.01)

(56) References Cited

U.S. PATENT DOCUMENTS

| | | | |
|---|---|---|---|
| 4,706,680 A | 11/1987 | Keusch et al. | |
| 5,042,481 A | 8/1991 | Suzuki et al. | |
| 5,224,479 A | 7/1993 | Sekine | |
| 5,343,869 A | 9/1994 | Pross et al. | |
| 5,458,124 A | 10/1995 | Stanko et al. | |
| 5,578,063 A | 11/1996 | Bocek et al. | |
| 5,622,168 A | 4/1997 | Keusch et al. | |
| 5,645,063 A | 7/1997 | Straka | |
| 5,819,741 A * | 10/1998 | Karlsson et al. | 600/523 |
| 5,951,598 A | 9/1999 | Bishay et al. | |
| 6,412,490 B1 * | 7/2002 | Lee | 128/897 |
| 6,453,186 B1 | 9/2002 | Lovejoy et al. | |
| 6,496,715 B1 * | 12/2002 | Lee et al. | 600/424 |
| 6,572,636 B1 | 6/2003 | Hagen et al. | |
| 6,730,025 B1 | 5/2004 | Platt | |
| 2003/0055478 A1 * | 3/2003 | Lyster et al. | 607/142 |
| 2003/0069510 A1 | 4/2003 | Semler | |
| 2003/0073915 A1 | 4/2003 | McLeod et al. | |
| 2003/0078510 A1 * | 4/2003 | Olson et al. | 600/510 |
| 2007/0032733 A1 * | 2/2007 | Burton | 600/509 |
| 2007/0167849 A1 * | 7/2007 | Zhang et al. | 600/509 |
| 2008/0027338 A1 * | 1/2008 | Lu et al. | 600/509 |
| 2010/0081913 A1 | 4/2010 | Cross et al. | |
| 2010/0228332 A1 * | 9/2010 | Hauge et al. | 607/142 |

FOREIGN PATENT DOCUMENTS

| | | |
|---|---|---|
| JP | 2002514107 A | 5/2002 |
| JP | 2005522284 A | 7/2005 |
| WO | 0222010 A | 3/2002 |
| WO | 2008068695 A1 | 6/2008 |

* cited by examiner

FIG. 15

REPOSITIONABLE ELECTRODE AND SYSTEMS AND METHODS FOR IDENTIFYING ELECTRODE POSITION FOR CARDIOTHERAPY

This invention relates to cardiotherapy and, more particularly, to adhesive electrodes for use in treating atrial fibrillation and other atrial arrhythmias and identification of an appropriate location on a patient for attaching the electrode.

Atrial fibrillation (AF) is a disorder found in about 22 million Americans. During atrial fibrillation, the heart's two small upper chambers (the atria) quiver instead of beating effectively due to random electrical activity within the muscle tissue of the atria. As a result, blood is not pumped completely out of them, so it may pool and clot. A blood clot in the atria can leave the heart and become lodged in an artery in the brain, causing a stroke. About 15 percent of strokes occur in people with atrial fibrillation.

In the early stages of AF, external cardioversion is often performed to restore normal heart rhythm. External cardioversion is typically performed using a defibrillator having a pair of electrodes positioned on the chest of the patient. A shock is delivered to the heart through the electrodes, disrupting the random electrical activity and causing the heart to return to a normal rhythm.

In cardioversion, the electrodes are coupled to a cardioverter having the combined functions of an ECG display screen and the electrical function of a defibrillator. A synchronizing function (either manually operated or automatic) based on the acquired ECG signal allows the cardioverter to deliver a reversion shock by way of the electrodes of a selected amount of electrical current over a predefined number of milliseconds at the proper moment in the cardiac cycle.

Inasmuch as cardioversion typically takes place over a period of time, the electrodes are usually adhered to the patient's chest, or the patient's chest and back. Recent studies have shown that proper positioning of the electrodes is important to the success of atrial defibrillation. However, adhesive electrodes are difficult to position properly inasmuch as once they are initially adhered on a patient's chest they cannot be readily repositioned to a better location if the initial location proves inadequate.

In view of the foregoing it would be advantageous to provide an adhesive electrode for treating heart arrhythmias that can be readily repositioned and a system and method for a treating physician to detect the proper location for the electrode.

In accordance with the principles of the present invention a system is provided for treating heart arrhythmia such as atrial fibrillation and atrial flutter. The system includes at least one electrode configured to be repositionable to a plurality of locations on a patient and conduct electrical activity therefrom. An electrocardiotherpy device is electrically coupled to the electrode. The device is operable to receive signals from the electrode, analyze the received signals, and generate human perceptible output indicative of the quality of the received signals from the plurality of locations.

Another aspect of the invention provides a method for positioning an electrode for cardiotherapy. The method includes analyzing signals from patient electrical activity for a plurality of electrode locations on a patient. Human perceptible output indicative of the quality of the signals for the plurality of locations is generated and a final electrode location on the patient for placement of the electrode for cardiotherapy is identified based on the human perceptible output.

In accordance with a further aspect of the present invention an electrode assembly includes a substrate and a conductor disposed on a lower surface of the substrate. An electrode is secured to the substrate. The electrode includes an upper surface contacting the conductor and a lower surface having first and second portions. The first portion has substantially greater adhesive strength than the second portion. A first release layer extending across and contacting the first portion and a second release layer extends across and contacts the second portion. The first portion may have an adhesive strength that is greater than two times that of the second portion.

In another aspect of the invention, an electrode assembly includes a substrate and a conductor disposed on a lower surface of the substrate. An electrode is secured to the substrate. The electrode includes an upper surface contacting the conductor and a lower surface. A conductive release layer contacts and extends across the lower surface.

In accordance with yet another aspect of the present invention an electrode assembly is provided that includes a substrate and a plurality of conductors disposed on a lower surface of the substrate. A plurality of electrodes each have an upper surface contacting one of the plurality of conductors and a lower surface. The lower surface has first and second portions. The first portion has a greater adhesive strength than the second portion. A first release layer extends across and contacts the first portion, and a plurality of second release layers each extend across and contact the second portion of one of the plurality of electrodes.

Figure 1:
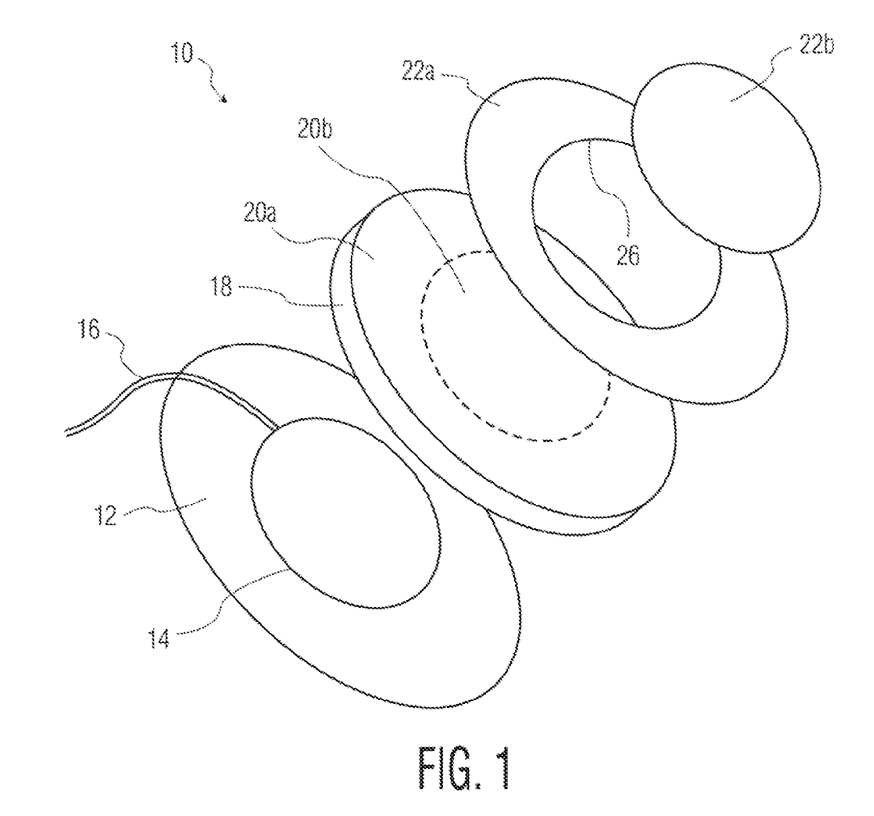
FIG. 1 is an exploded view of a repositionable electrode assembly in accordance with an embodiment of the present invention.

Referring to FIG. 1, an electrode assembly 10 for use with a cardioverter or defibrillator includes a substrate 12 preferably formed of a flexible material such as plastic, however, in some embodiments, the substrate 12 may be rigid. A conductor 14 is secured to a lower surface of the substrate 12. The conductor 14 typically is formed from a thin material such as layer of conductive ink or metal foil. For example, the conductor 14 may consist of silver/silver-chloride ink or a thin layer (e.g. about 2 mil) of tin. The conductor 14 may cover all or part of the lower surface. In the illustrated embodiment, the conductor 14 covers a central portion of the lower surface of the substrate 12. In some embodiments, multiple conductors 14 electrically isolated from one another are secured to the lower surface of the substrate 12. One or more wires 16 are coupled to the one or more conductors for transferring electrical signals to and from the one or more conductors 14.

An electrode 18 is secured to the lower surface of the substrate 12 and the conductor 14, such as by means of an adhesive. The electrode 18 may likewise cover all or part of the lower surface and may occupy an area equal to or greater or smaller than that occupied by the conductor 14. In embodiments having multiple conductors 14, multiple electrodes 18 electrically isolated from one another may alternatively be used. In such embodiments, an insulator, such as a foam having a thickness less than or equal to that of the electrodes 18 may be positioned in spaces between and around the electrodes 18. In embodiments having multiple electrodes 18, the electrodes 18 preferably are sized such that they may be positioned on the lower surface having each electrode contacting only one conductor 14.

The electrode 18 is formed of a material suitable for conducting electrical signals to and from a patient's skin. In the illustrated embodiment, the electrode 18 comprises a hydrogel.

The lower surface of the electrode of FIG. 1 includes first and second portions 20a, 20b. In the illustrated embodiment, the first portion 20a surrounds the second portion 20b, though other arrangements are contemplated by the invention, such a second portion 20b extending across the center of the electrode 18 with the first portion 20a including portions located on either side of the second portion 20b.

One of the first and second portions 20a, 20b is substantially more adhesive than the other. In some embodiments, the less adhesive of the first and second portions 20a, 20b bears no adhesive and is no more adhesive than the hydrogel material from which it is formed. In other embodiments, the less adhesive of the first and second portions 20a, 20b bears an adhesive that is formulated or applied such that its adhesive strength is much less than the adhesive strength of the more adhesive portion. For example, the more adhesive of the first and second portions 20a, 20b may be greater than twice as adhesive as the other portion 20a, 20b. In the illustrated embodiment, it is the outer portion 20a that is more adhesive than the inner portion 20b.

Figure 2:
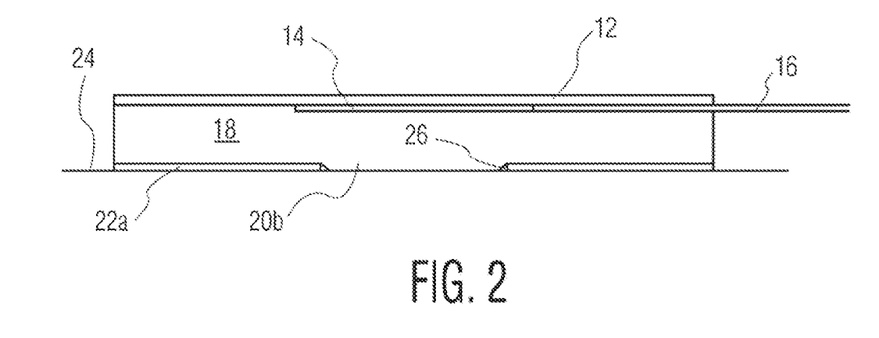
FIG. 2 is a side cross-sectional view of the electrode assembly of FIG. 1.

Referring to FIGS. 1 and 2, a first release layer portion 22a is releasably secured to the first portion 20a and a second release layer portion 22b is releasably secured to the second portion 20b. In use, an operator will remove the release layer portion 22b over the less adhesive portion 20b in order to test different positions on a patient's thorax before finally adhering the electrode assembly 10 to the patient using the more adhesive portion 20a. As shown in FIG. 2, during use the operator will remove the release layer portion 22b to expose the less adhesive portion 20b. The less adhesive portion 20b then can be placed in contact with a patient's skin 24 through an aperture 26 in the release layer portion 22a in order to provide electrical coupling to a defibrillator or monitoring device.

In some embodiments, the release layer portions 22a, 22b correspond in size and relative location to the adhesive portions 20a, 20b. In other embodiments, the release layer portion 22b is coextensive with the release layer portion 22a and the less adhesive portion 20b is exposed through the aperture 26 when the first release layer 22b is removed. As is customary in the art, the release layers may have tabs extending therefrom which may be grasped by a user to peel the release layers from the respective electrode portions.

Although some embodiments include adhesive portions 20a, 20b having different adhesive strengths, in other embodiments the adhesive portions 20a, 20b have substantially equal adhesive strength, i.e., they each receive the same adhesive coating. The electrode is then used with a smaller adhesive area when being repositioned and, when the desired location for the electrode is identified, the remainder of the adhesive is exposed and the full adhesive area of the electrode is used to secure the electrode in its finally determined location on the body. In such embodiments, the first and second release layer portions 22a, 22b may be used such that one of the adhesive portions 20a or 20b is exposed while leaving the other adhesive portion covered by the other release layer portion. In this manner, the electrode assembly 10 may be adhered at various locations, while preserving an adhesive portion 22a or 22b for longer-term securing, of the electrode assembly 10 to the patient, inasmuch as repeated adhesion and removal tends to reduce the adhesive strength of the first exposed adhesive portion 20a, 20b.

Figure 3:
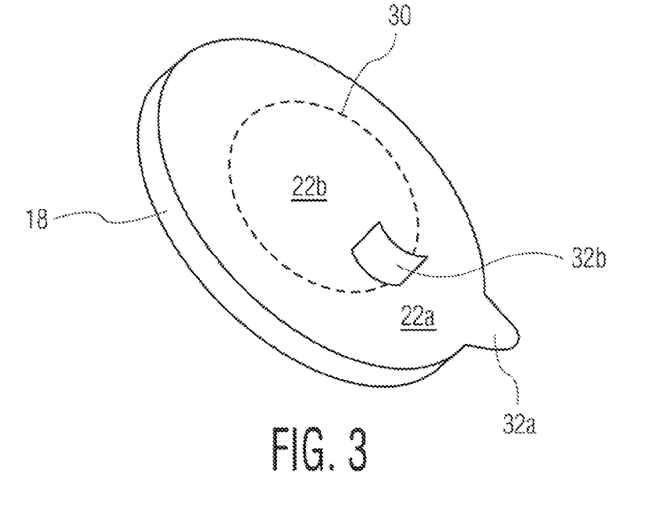
FIG. 3 is an isometric view of an alternative embodiment of an electrode assembly in accordance with an embodiment of the present invention.

Referring to FIG. 3, in other embodiments, the release layer portions 22a, 22b are firmed of a monolithic sheet of material having perforations or otherwise weakened area 30 at the boundary between the release layer portions 22a, 22b, such that the release layer portion 22b can be readily separated from the release layer portion 22a while leaving the release layer portion 22a adhered to the adhesive portion 20a. A tab 32b may be secured to the release layer portion 22b as shown in the drawing. An operator grasps the tab 32b to peel the release layer portion 22b from the adhesive portion 20b without removing the release layer portion 22a. When the desired location for the electrode is found, the riser grasps the tab 32a, here shown as integral to release layer portion 22a, to remove release layer portion 22a.

Figure 4:
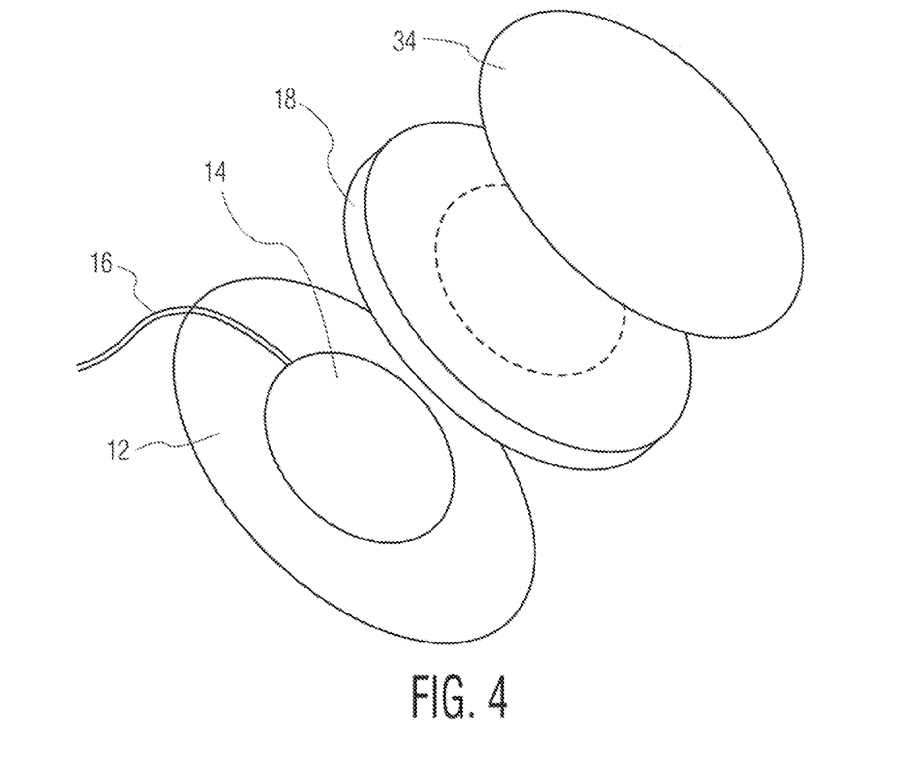
FIG. 4 is an exploded view of an alternative embodiment of an electrode assembly in accordance with an embodiment of the present invention.
Figure 5:
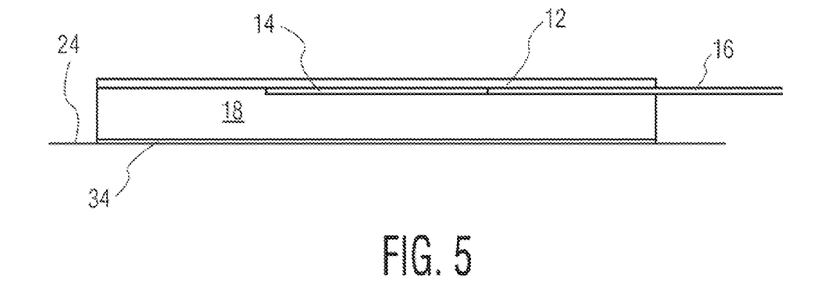
FIG. 5 is a side cross-sectional view of the electrode assembly of FIG. 4.
Figure 6:
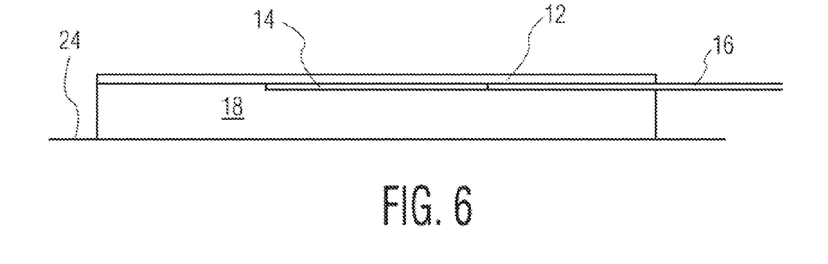
FIG. 6 is a side cross sectional view of the electrode assembly of any of the preceding figures adhered to a patient's skin in accordance with an embodiment of the present invention.

Referring to FIG. 4, in this embodiment a release layer 34 contacts and extends across the lower surface of the electrode 18. The release layer 34 includes a conductive material such that electrical signals are conducted from the lower surface of the release layer 34 to its upper surface. In the illustrated embodiment, the release layer 34 includes a metal foil. In other embodiments, conductive ink is printed on the upper and lower surfaces of the release layer 34 such that the conductive ink of the upper surface is in contact with the electrode 18 and with the conductive ink of the lower surface at the edges of the release layer 34. Referring to FIG. 5, during repositionable use, the operator presses the release layer 34 to the patient's skin 24. Electrical signals are then conducted through the release layer 34 to the electrode 18. The electrode can be repositioned until the desired location is found, at which time the release layer 34 is removed and the electrode adhered to the skin by the adhesive hydrogel layer 18. Referring to FIG. 6, once a desired position on the patient is located, the operator removes the release layer 34 of the embodiment of FIG. 5. The electrode assembly 10 is then adhered to the patient's skin using the adhesive lower surface of the electrode 18 or the more adhesive portion 20a, 20b of the lower surface of the electrode 18.

Figure 7:
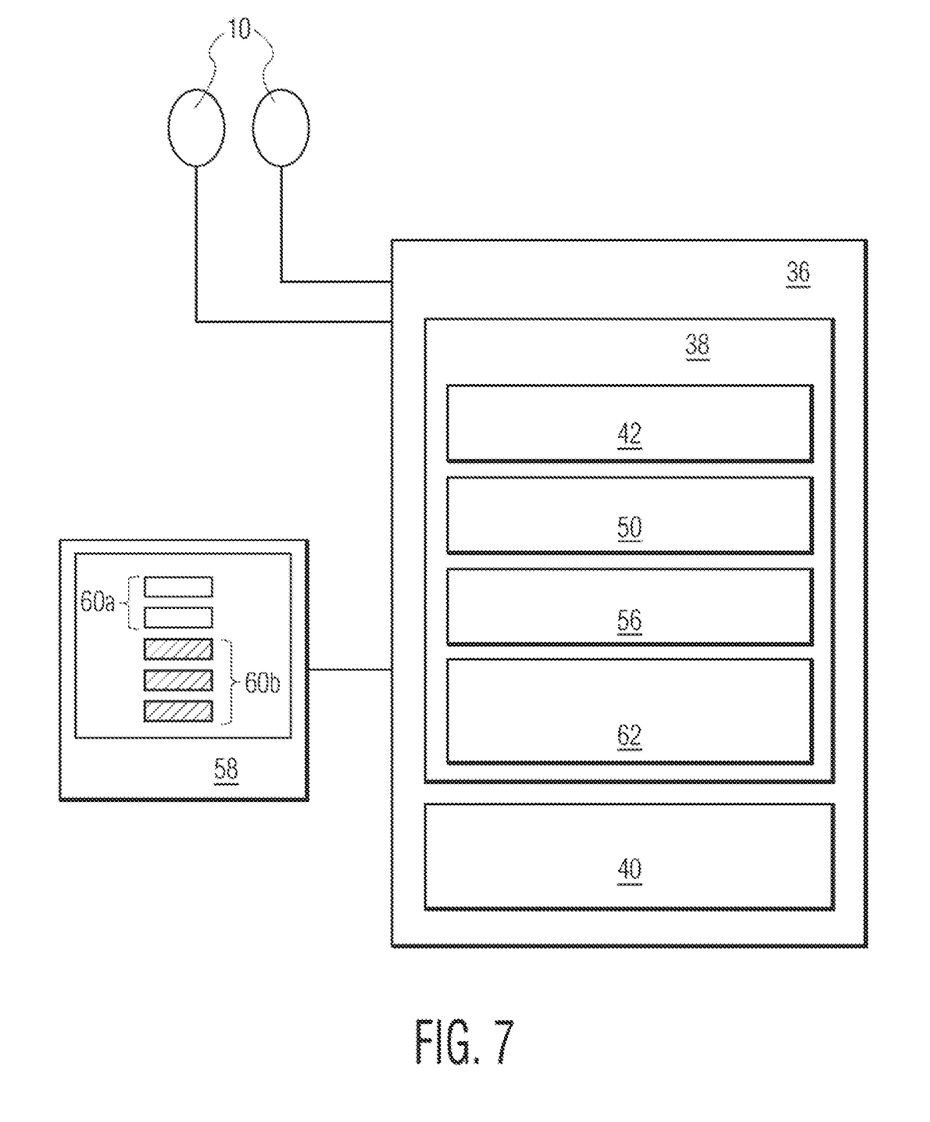
FIG. 7 is a schematic block diagram of a cardioverter system in accordance with an embodiment of the present invention.

Referring to FIG. 7, the electrode assemblies 10 as previously described may be used with a cardioverter or defibrillator 36 including a controller 38 and an external or internal power source 40 such as a battery. The controller 38 includes a signal processing module 42 for receiving signals from the electrode assemblies 10. The signal processing module 42 processes the received signals to remove noise and other artifacts.

Figure 8:
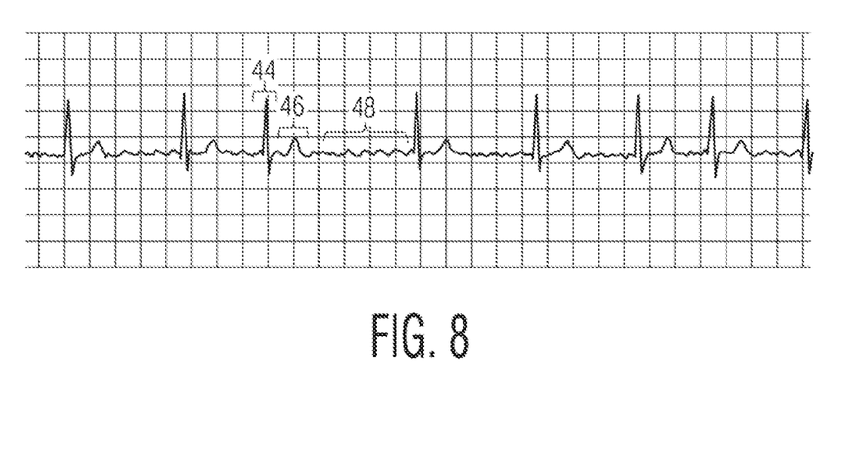
FIG. 8 illustrates an electrocardiogram of a heart experiencing atrial fibrillation.

Referring to FIG. 8 the signal processing module 42 further processes the received signals to extract relevant data from the signal. The electrical activity of a heart experiencing AF is shown in the ECG signal of FIG. 8. The QRS complex 44 during AF may be normal and readily discernable as can the I' wave 46. However, during AF, the P-wave corresponding to contraction of the atria is replaced by disorganized activity shown in segment 48 between the T wave and the succeeding QRS complex.

Accordingly, the signal processing module 42 may isolate portions of the received signals corresponding to atrial fibrillation by outputting only the segment 48 preceding the QRS complex 44 such that the function of the atria may be analyzed. In some embodiments, the signal processing module 42 outputs the region 48 located between the QRS complexes 44 and T waves 46. The QRS complexes 44 and T waves 46 may be identified by the signal processing module 42 according to electrocardiogram (ECG) analysis methods known in the art. In some embodiments, the signal processing module 42 removes portions of the received signals corresponding to ventricular fibrillation.

The controller 38 (FIG. 7) further includes a locating module 50 for aiding an operator in identifying a suitable location for positioning the electrode assemblies 10. Studies have shown that the positions of the electrode assemblies 10 during cardioversion is important to the success of the treatment. Accordingly, the locating module 50 analyzes the received signals to identify when the signals indicate that an electrode assembly 10, or both electrode assemblies 10, are positioned at a suitable location for treating AF. In some embodiments, the locating module 50 analyzes the amplitude of waves within the segments 48 (FIG. 8) and compares the amplitude to a threshold amplitude and identities those locations at which the received signals within the segments 48 exceeded the threshold amplitude as suitable locations. In some embodiments, the locating module 50 records the received signals over a first period of time and identifies a maximum amplitude within the segments 48. During a second period of time following the first period of time, the locating module 50 identifies locations at which the amplitude within the segments 48 exceeds or approximates the maximum amplitude as more suitable locations.

Figure 9:
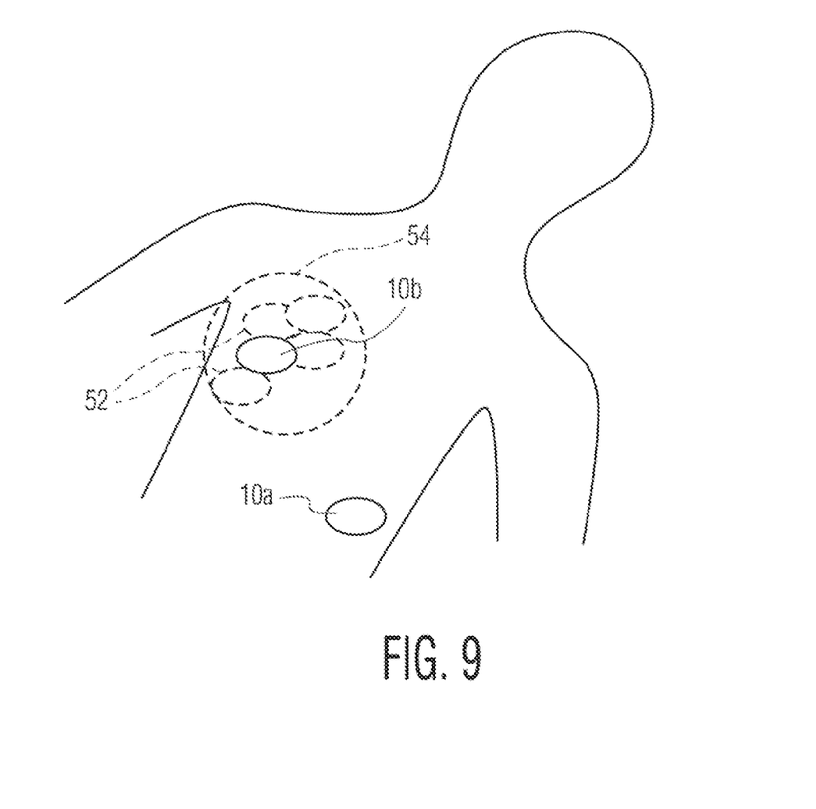
FIG. 9 illustrates the process of positioning a repositionable electrode on a patient in accordance with an embodiment of the present invention.

Referring to FIGS. 7 and 9, in use the operator will adhere one of the electrode assemblies 10 to the patient. In this example the operator has adhered electrode assembly 10a to the left side of the patients rib cage at the apex of the heart with its more adhesive or entire electrode portion. The operator will then remove the second release layer portion 22b (or leave the conductive release layer 34 in contact with the electrode 18) from the less adhesive portion of the second electrode assembly 10b and place it in contact with various locations 52 in the general areas 54 on the patient's upper right thorax in which current knowledge indicates the second electrode assembly 10b should be placed to treat AF. As the second electrode assembly 10b is moved, the locating module 50 analyzes the received signals to identify which of the locations 52 is relatively more suitable than the other locations. In the illustrated embodiment the electrodes 10 are arranged in an anterior-apex configuration as known in the art. In other uses, the electrodes 10 are arranged in the anterior-posterior configuration in which one electrode 10 is adhered to the patient's back below the scapula and the other is positioned near the patient's sternum. In a preferred method of use, an electrode is adhered to the apical or posterior portion first and then a suitable anterior position is identified according to the apparatus and method disclosed herein.

In some embodiments, the locating module 50 identifies the more suitable location 52 in a two stage process. In the first stage, the operator moves the electrode 10b within the general area 54 and the locating module 50 records the received signals and extracts a maximum amplitude for the segments 48 recorded during the first stage. In the second stage, the electrode 10 is again moved to various locations 52 within the general area 54, and when the locating module 50 receives signals having an amplitude proximate, equal, or exceeding the previously determined maximum amplitude, it produces an output indicating that the new location 52 from which the signals are received is a more suitable location. In this manner, the location 52 selected by the locating module 52 is determined based on each individual patient rather than a fixed threshold. It is also possible to effect accurate electrode placement by successive approximation, placing one electrode, then the other electrode then adjusting the position of one or both electrodes to achieve the best final placement for both electrodes.

Referring again to FIG. 7, an output module 56 of the controller 38 receives the output of the locating module 50 and produces a human perceptible output communicating to the operator that the most recent location 52 is the more suitable location for the electrode 10b. The human perceptible output may be an audible alarm or verbal message produced by a speaker coupled to the controller 38 or information displayed on a display 58 coupled to the controller 38.

In some embodiments, the output module 56 produces an output proportional to a peak amplitude, average amplitude, or other metric of the segments 48 in the ECG corresponding to atrial activity. In such embodiments, the locating module 50 may be omitted in reliance on operator judgment. For example, the display 58 may output bars 60a, 60b, with the height of the column of bars 60a, 60b corresponding to the amplitude or other metric Bars 60a above a threshold may have a different color or other visual characteristic than bars 60b below the threshold, communicating to the operator that when bars 60a are displayed, the location of the electrode assembly 10 is likely adequate. Other indicators are possible for showing the amplitude of detected atrial electrical activity, such as a dial indicator, digital display, or the like. In use the operator will move the electrode assembly 10b to various positions while monitoring the display 58 and observing the maximum height of the column of bars 60a, 60b. The electrode assembly 10 may then be adhered at the maximum, or near maximum, position identified by the operator.

When a suitable location is found, the operator removes the first release portion 22a from the more adhesive portion, or release layer 34, and adheres the electrode assembly 10 at or near the location 52 identified according to one of the methods described above. A cardioversion/defibrillation module 62 may then control the timing and magnitude of one or more electrical shocks to the patient through the electrode assemblies 10 as known in the art.

Figure 10:
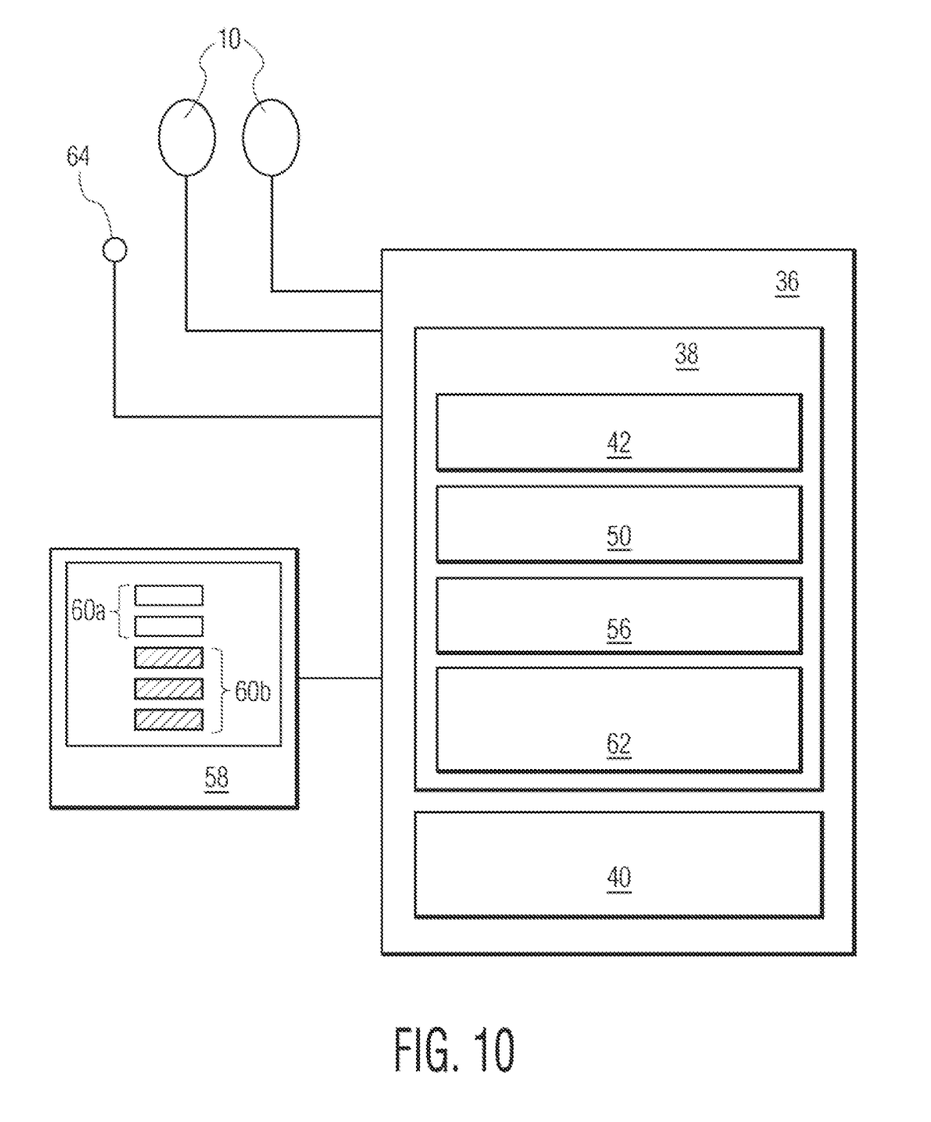
FIG. 10 is a schematic block, diagram of another cardioverter system in accordance with an embodiment of the present invention.

Referring to FIG. 10, in this embodiment a cardioverter/defibrillator 36 includes electrode assemblies 10 having an adhesive electrode and a single release layer covering the adhesive lower surface of the electrode. One or more test electrodes 64 are used having a non-adhesive lower surface, or a lower surface that is relatively less adhesive than the lower surface of the electrode assemblies 10. In such embodiments, the test electrode 64 is moved over the tentative locations 52 while one of the electrode assemblies 10 is secured to the other area of the patient. The locating module 50 analyzes signals from the test electrode 64 to determine which of the locations 52 is more suitable for adhering the other electrode assembly 10. When the locating module 50 identifies a location, the operator then removes the release layer from the electrode assembly 10 and adheres it to the patient's thorax at the more suitable location.

Figure 11:
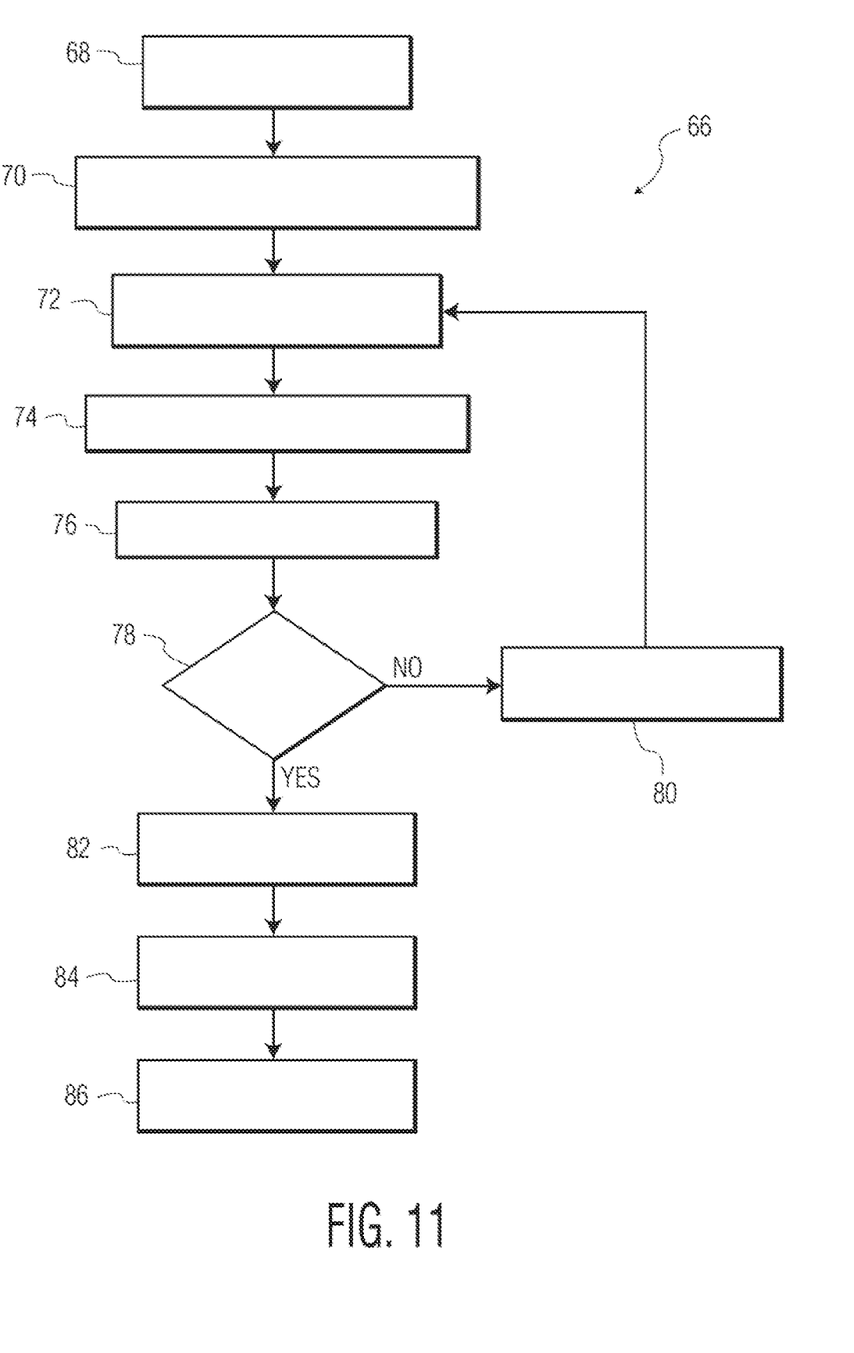
FIG. 11 is a flow diagram of a first method for using a repositionable electrode in accordance with an embodiment of the present invention.

Referring to FIG. 11, a method 66 for positioning an electrode assembly includes adhering a first electrode to the patient at step 68. In a preferred embodiment, the first electrode is secured in the posterior or apical position. At step 70 a first electrode portion of an anterior electrode is exposed. At step 72, the first electrode portion is placed in contact with a patient. At step 74, electrical activity passing through the electrode portion is measured. At step 76, the electrical activity is analyzed to determine the amplitude of electrical activity corresponding to AF. At step 78, the method 66 includes evaluating whether the location where the first electrode portion was placed at step 72 is adequate. Step 78 may include comparing the amplitude of electrical activity corresponding to AF to a threshold or to a maximum amplitude value recorded during other measurements of electrical activity corresponding to AF. If the amplitude at a location is greater than the threshold or maximum amplitude value, then the location may be deemed adequate at step 78, in some embodiments, step 78 is performed by an operator evaluating the output of the display 58 and deciding whether a location is adequate based on preceding outputs from the display 58 as discussed above.

If at step 78 it is determined that the location is not adequate, the first electrode portion is re-positioned at step 80 and steps 72-78 are then repeated. If at step 78 it is determined that a location is adequate, then a second electrode portion is exposed at step 82, with the second electrode portion being substantially more adhesive than the first electrode portion. In some embodiments, the second electrode portion has an adhesive strength greater than twice that of the first electrode portion. At step 84, the anterior electrode is adhered to the patient using the second electrode portion. At step 86, cardioversion is performed by passing electrical current through the electrodes.

Figure 12:
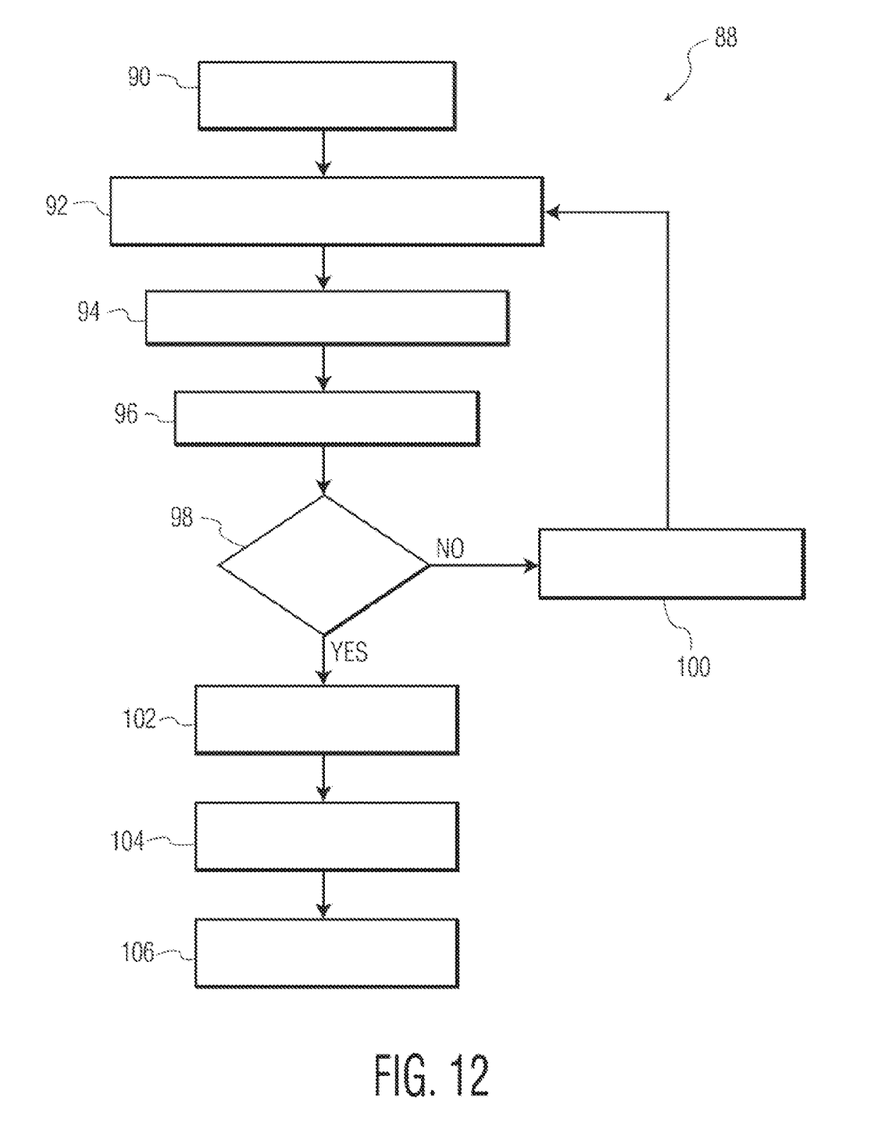
FIG. 12 is a flow diagram of a second method for using a repositionable electrode in accordance with an embodiment of the present invention.

Referring to FIG. 12, another method 88 for positioning an electrode includes adhering an electrode to the patient at a posterior or apical position at step 90. At step 92, a conductive release layer of an anterior electrode is contacted with the patient. At step 94, electrical activity passing through the electrode portion is measured. At step 96, the electrical activity is analyzed to determine the amplitude of electrical activity corresponding to AF. At step 98, the method 88 includes evaluating whether the location where the anterior electrode was placed at step 92 is adequate. Step 98 may include comparing the amplitude of electrical activity corresponding to AF to a threshold or to a maximum amplitude value recorded during other measurements of electrical activity corresponding to AF. If the amplitude at a location is greater than the threshold or maximum amplitude value, then the location may be deemed adequate at step 98. If at step 98 it is determined that the location is not adequate or inferior to a prior location, the anterior electrode is re-positioned at step 100 and steps 92-98 are then repeated. In some embodiments, step 98 is performed by an operator evaluating the output of the display 58 and deciding whether a location is adequate or improved based on preceding outputs from the display 58 as discussed above.

If at step 98 it is determined that a location is adequate or the most adequate, the conductive release layer is removed to expose the adhesive electrode surface at step 102. At step 104, the anterior electrode is adhered to the patient using the second electrode portion. At step 106, cardioversion or defibrillation is performed by passing electrical current through the electrodes.

Figure 13:
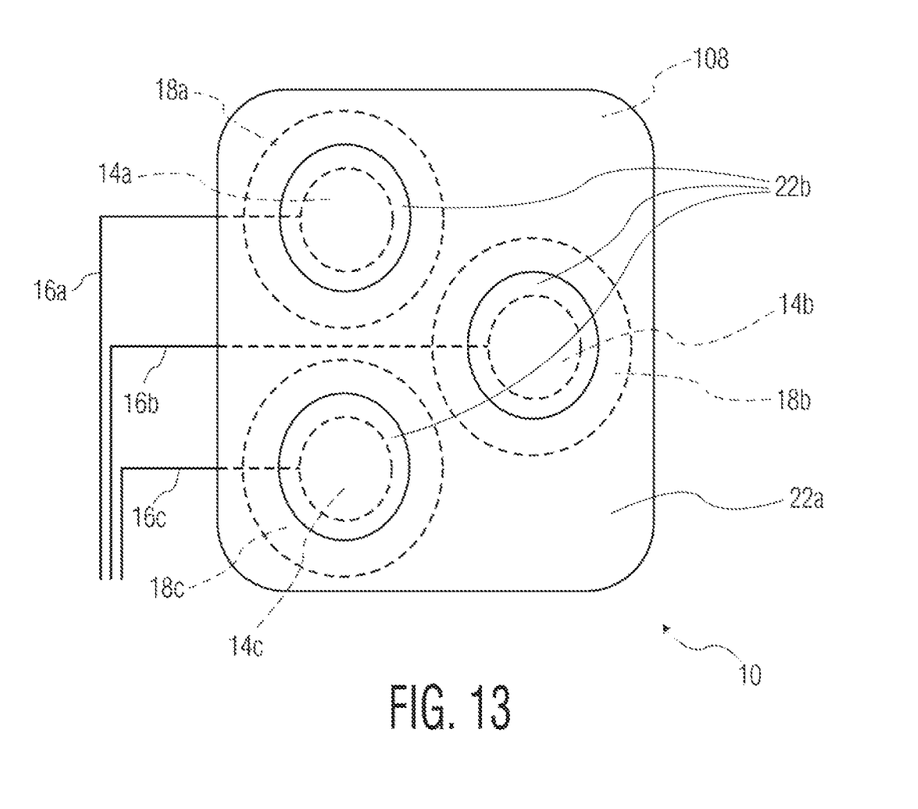
FIG. 13 is a bottom view of a multi-electrode electrode assembly in accordance with an embodiment of the present invention.
Figure 14:
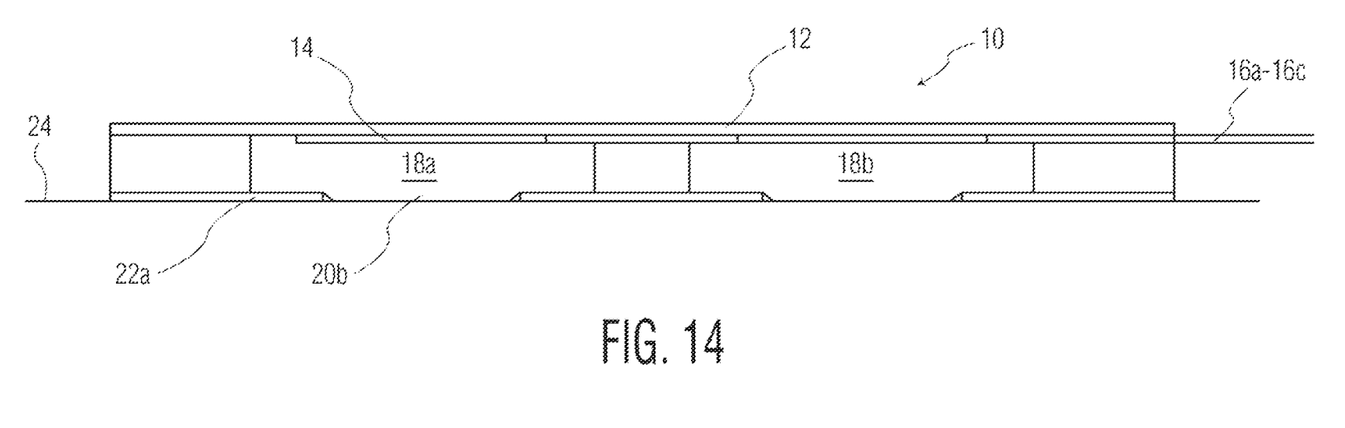
FIG. 14 is a side cross-sectional view of the multi-electrode assembly of FIG. 13.

Referring to FIGS. 13 and 14, in an another embodiment the electrode assembly 10 includes multiple electrodes 18a-18c each positioned over a corresponding conductor 14a-14c. Wires 16a-16c are coupled to each of the electrodes. The electrodes 18a-18c may be electrically isolated from one another, such as by a foam layer 108 having apertures sized to receive the electrodes 18a-18e. The foam layer 108 may have a thickness that is equal or less than that of the electrodes 18a-18c such that the lower surface of the electrodes is either flush with or protrudes from the foam layer 108.

The release layer may include a first release layer portion 22a covering, adhesive portions of the electrodes 18a-18c and the foam layer 108. In the illustrated embodiment, the first release layer portion 22a covers the adhesive portions of all the electrodes 18a-18c as well as areas between the electrodes 18a-18c. However, in other embodiments, individual first release layer portions 22a cover the adhesive portions of each electrode 18a-18c. In still other embodiments, the electrodes 18a-18c are not adhesive whereas the lower surface of the foam layer 108 is adhesive. In such embodiments, the first release layer 22a may extend only over the foam layer 108. In the embodiment of FIG. 13, multiple second release layer portions 22b cover the non-adhesive portions of the electrodes 18a-18c or the entire electrodes 18a-18c.

Figure 15:
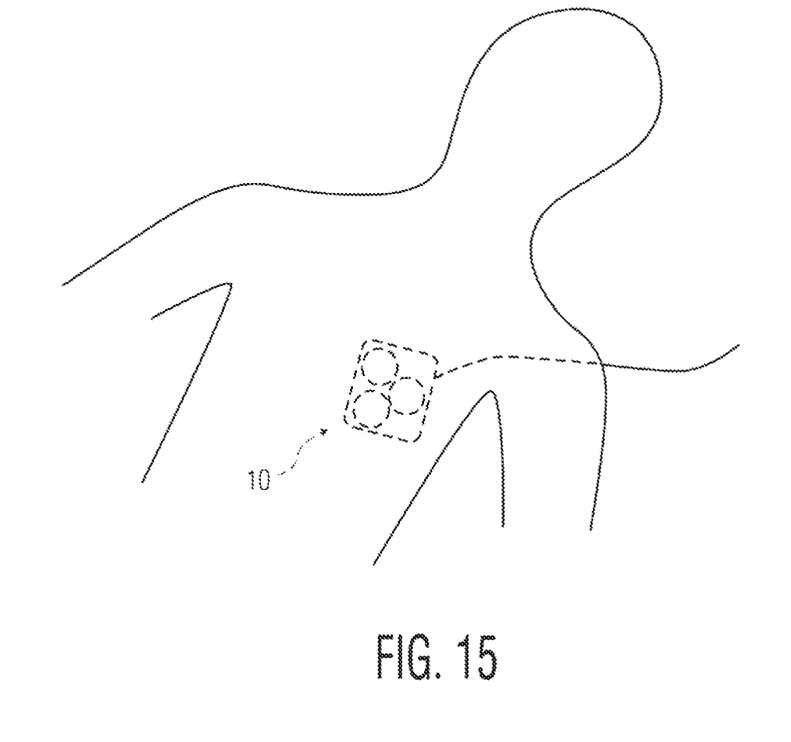
FIG. 15 is a top view of the electrode assembly of FIG. 14 in use on a patient in accordance with an embodiment of the present invention.

Referring to FIG. 15, as in the embodiments discussed above, the operator will typically remove the second release layer portions 22b in order to probe different locations without adhering the electrode assembly 10 to the patient. Once a suitable location is found, the operator will then remove the first release layer portion 22a to expose the adhesive portions of the electrodes 18a-18c or the adhesive lower surface of the foam layer 108 and adhere the electrode assembly 10 to the patient.

The embodiment of FIG. 13 provides the advantage that it does not require that a second electrode assembly be adhered to the patient in order to perform monitoring or measurement. Instead, the separate electrodes of the assembly of FIG. 13 will provide this function. Accordingly, the electrode assembly of FIG. 13 may be used to locate a position for a first electrode. An electrode according to any of the above described embodiments may then be used as the second electrode. In this manner both electrodes may be positioned with reference to the electrical activity of the patient's heart at a chosen location. In a preferred method of use, a first electrode assembly 10 according to the embodiment of FIG. 13 is first positioned at the posterior position as shown in FIG. 15. A second electrode according to any of the above described embodiments is then used to locate a suitable anterior position on the patient's chest according to any of the above described methods using signals from the first electrode assembly as a reference.

Wires 16a-16c extending from each of the conductors 14a-14c couple to a cardioverter 36 or a monitoring device. The cardioverter 36 receives the signals from the wires 16a-16c and may calculate differences between the signals measured by an electrode 18a-18c and each of the other electrodes 18a-18c. These differences may then be summed, averaged, or otherwise combined. In some embodiments, the sign of the differences is modified such they are all of the same polarity prior to combining. The combined signals may then be used to produce a human perceptible output for an operator. The operator may use the combined signals to identify the location on the patient for which the magnitude of the combined signals was high relative to other locations. The operator may then remove the first release layer 22a and adhere the electrode assembly 10 to the patient at that location. Following adhesion of the electrode assembly 10 to the patient, each of the electrodes 18a-18c may be coupled to a common signal line such that they function as a single electrode for cardioversion.

From the foregoing it will be appreciated that, although specific embodiments of the invention have been described herein for purposes of illustration, various modifications may be made without deviating from the spirit and scope of the invention. For example, one of the electrode assemblies such as that intended for posterior or apical attachment may be a standard electrode with a single adhesive surface not designed for reattachment, and only the second electrode need have the repositionable functionality. The different electrodes can be indicated by different symbology as shown in U.S. Pat. No. 5,951,598 (Bishay et al.) Reference to modules constituting embodiments of the invention indicate structures and steps for performing the functions attributed to a module, however the structures for performing the functions attributed to a module may be operate at different times or include multiple distinct structures that may or may not be co-located. Accordingly, the invention is not limited except as by the appended claims.

What is claimed is:

1. A system for treating heart arrhythmia comprising:
    at least one electrode configured to be repositioned to a plurality of locations on a patient's skin and conduct electrical activity corresponding to the patient, wherein the electrode further comprises
    a substrate,
    a conductor disposed on a lower surface of the substrate,
    an electrode having an upper surface contacting the conductor, the electrode adapted to conduct electrical signals to and from a patient's skin,
    an adhesive lower surface of the electrode, and
    first and second release layers having a non-adhesive upper surface extending across portions of the adhesive surface, the release layers comprising a non-conductive material; and
    an electrocardiotherapy device electrically coupled to the electrode, the device operable to receive signals corresponding to the electrical activity from the electrode, analyze the received signals, and generate human perceptible output indicative of the quality of the received signals from the plurality of locations,
    wherein the electrocardiotherapy device comprises a controller operable to measure a patient ECG from the received signals and further operable to analyze the patient ECG and calculate a measure for atrial signal component strength to generate the human perceptible output indicative of the quality of the received signals,
    wherein the electrocardiotherapy device comprises a defibrillator.

2. The system of claim 1, wherein the controller is operable to
    calculate a measure for the atrial signal component strength based on the amplitude of the atrial signal component of an ECG signal.

3. The system of claim 2, wherein the controller is operable to calculate a measure for the atrial signal component strength based on the amplitude of the atrial signal component relative to a threshold amplitude.

4. A method for positioning an electrode for cardiotherapy comprising:
    analyzing atrial-related signals from patient electrical activity for a plurality of electrode locations on a patient;
    generating human perceptible output indicative of the quality of the atrial-related signals for the plurality of locations;
    removing a first release layer of the electrode to expose a conductive portion and repositioning the electrode to different locations on the patient to obtain atrial-related signals from patient electrical activity therefrom;
    identifying a final electrode location on the patient for placement of the electrode for cardiotherapy based on the human perceptible output; and
    removing a second release layer of the electrode to expose an adhesive portion and adhering the electrode to the final electrode location on the patient.

5. The method of claim 4, wherein analyzing signals from patient electrical activity comprises:
    measuring patient ECG;
    analyzing the patient ECG; and
    calculating a measure for atrial signal component strength of the patient ECG.

6. The method of claim 5, wherein calculating the measure for the atrial signal component strength is based on the amplitude of the atrial signal component.

7. The method of claim 6, wherein calculating the measure for the atrial signal component strength is based on the amplitude of the atrial signal component relative to a threshold amplitude.

8. A system for treating heart arrhythmia comprising:
    at least one electrode configured to be repositioned to a plurality of locations on a patient's skin and conduct electrical activity corresponding to the patient, wherein the electrode further comprises
    a substrate,
    a conductor disposed on a lower surface of the substrate,
    an electrode having an upper surface contacting the conductor, the electrode adapted to conduct electrical signals to and from a patient's skin,
    an adhesive lower surface of the electrode, and
    a release layer having a non-adhesive upper surface extending across the adhesive surface, the release layer comprising a conductive material extending from the upper surface to a lower surface thereof and contacting the electrode; and
    an electrocardiotherapy device electrically coupled to the electrode, the device operable to receive signals corresponding to the electrical activity from the electrode, analyze the received signals, and generate human perceptible output indicative of the quality of the received signals from the plurality of locations,
    wherein the electrocardiotherapy device comprises a controller operable to measure a patient ECG from the received signals and further operable to analyze the patient ECG and calculate a measure for atrial signal component strength to generate the human perceptible output indicative of the quality of the received signals,
    wherein the electrocardiotherapy device comprises a defibrillator.

* * * * *